(12) United States Patent
Sassoon

(10) Patent No.: US 8,048,379 B2
(45) Date of Patent: Nov. 1, 2011

(54) MULTI CARTRIDGE AIR FRESHENER

(75) Inventor: Simon Sassoon, New York, NY (US)

(73) Assignee: Hyso Technology LLC, Carlstadt, NJ (US)

( * ) Notice: Subject to any disclaimer, the term of this patent is extended or adjusted under 35 U.S.C. 154(b) by 374 days.

(21) Appl. No.: 12/464,690

(22) Filed: May 12, 2009

(65) Prior Publication Data

US 2010/0061896 A1  Mar. 11, 2010

Related U.S. Application Data

(60) Provisional application No. 61/094,641, filed on Sep. 5, 2008, provisional application No. 61/105,056, filed on Oct. 14, 2008.

(51) Int. Cl.
| | |
|---|---|
| A61L 9/00 | (2006.01) |
| A62B 7/08 | (2006.01) |
| A01M 13/00 | (2006.01) |
| A24F 25/00 | (2006.01) |
| B65D 73/00 | (2006.01) |
| B65D 1/24 | (2006.01) |
| B01D 47/00 | (2006.01) |
| B01D 39/00 | (2006.01) |
| F02M 15/04 | (2006.01) |
| A47G 19/00 | (2006.01) |
| A47F 1/04 | (2006.01) |

(52) U.S. Cl. ............. 422/124; 422/1; 422/5; 422/120; 422/123; 422/306; 422/900; 239/51.5; 239/53; 239/54; 239/55; 239/56; 239/57; 239/58; 239/59; 239/60; 261/26; 261/104; 261/142; 261/DIG. 65; 261/DIG. 88; 261/DIG. 89; 261/72 R; 220/23.83; 220/500; 220/998; 221/66; 221/92; 221/154; 221/156; 221/186; 221/197; 96/226; 43/1; 43/125; 206/485

(58) Field of Classification Search ................. 422/1, 5, 422/120, 123–124, 306, 900; 239/51.5, 53–60; 261/26, 104, 142, DIG. 65, DIG. 88, DIG. 89, 261/72 R; 220/23.83, 500, 998; 221/66, 221/92, 154, 156, 186, 197; 96/226; 43/1, 43/125; 206/485

See application file for complete search history.

(56) References Cited

U.S. PATENT DOCUMENTS 4,252,547 A * 2/1981 Johnson ........................ 96/121

* cited by examiner

Primary Examiner — Jill Warden
Assistant Examiner — Monzer Chorbaji
(74) Attorney, Agent, or Firm — Leason Ellis LLP

(57) ABSTRACT

An air freshener includes a housing having at least a first compartment and a second compartment, each of the first and second compartments having vents. The air freshener includes a first fan unit disposed within the first compartment and a second fan unit disposed within the second compartment. The air freshener also includes a first fragrance emitting substance disposed within the first compartment proximate the first fan unit and a second fragrance emitting substance disposed within the second compartment proximate the second fan unit. A programmable processor is operatively connected to a power source and the first and second fan units and configured to drive at least one of the first and second fan units so as to promote discharge of one of the first and second fragrance emitting substances from the housing.

17 Claims, 8 Drawing Sheets

MULTI CARTRIDGE AIR FRESHENER

CROSS-REFERENCE TO RELATED APPLICATIONS

The present application claims the benefit of U.S. patent application Ser. No. 61/105,056, filed Oct. 14, 2008, and U.S. patent application Ser. No. 61/094,641, filed Sep. 5, 2008, each of which is hereby incorporated by reference in its entirety.

TECHNICAL FIELD

The present invention relates to an air freshener apparatus, and more particularly, to a symmetrical apparatus that include two or more cartridges that each includes an air freshener mixture to be controllably emitted into the air for freshening the air of any room and permits different fragrances to be emitted at controlled times.

BACKGROUND

Air fresheners are found in most homes and businesses and are consumer products that mitigate unpleasant odors in indoor spaces. Air fresheners can come in a number of different forms, including but not limited to, candles, aerosol sprays, potpourri, gels and mechanical or heat release products. Air fresheners work in a number of different ways, including (a) absorption, where absorbent materials, such as activated charcoal, is used to be absorb offending chemical odors; (b) disinfection, where odors caused by bacterial activity can be eliminated by disinfectants like ozone or bleaching agents; (c) anesthetization, where anesthetics dull the sense of smell and (d) masking, where odors are obscured with a fragrance. The last type is the most common in terms of placement in a home and public rooms, such as public restrooms.

However, common household air fresheners have come under fire recently from a number of activist groups and even governmental bodies and councils. For example, a National Resources Defense Council (NRDC) study of thirteen of the more common household air fresheners found that most of these products contain chemicals that can aggravate asthma and affect reproductive development. The NRDC called for more rigorous supervision of the manufacturers and their products, which were widely assumed to be safe. One of the more troubling findings was that lab testing confirmed the presence of phthalates, or hormone-disrupting chemicals that may pose a particular health risk to babies and young children. Many of these products were marked "all natural" and none of the products had these chemicals listed on their labels. There are many movements by health and safety groups to make people more aware of the presence of volatile organic compounds (VOCs) in everyday consumer products, such as air fresheners. Since these compounds may be harmful to one's health over time, there is a need for alternative products.

Another problem when using a commercial air freshener is the fact that your entire house seem to smell like a bathroom—which is far from desirable. Since commercial air fresheners are most often used in bathrooms or in closets or laundry rooms, they are designed and geared towards this use. There is thus a need and desire to provide an improved air freshener that offers a wider variety of pleasant smelling fragrances that can be customized according to a particular person's needs or desires.

Over the recent years, there is a growing trend in natural aromatherapy products and services. Aromatherapy is a form of alternative medicine that uses volatile liquid plant materials, known as essential oils (EOs), and other aromatic compounds from plants for the purpose of affecting a person's mood or health. Essential oils differ in chemical composition from other herbal products because the distillation process only recovers the lighter phytomolecules. For this reason essential oils are rich in monoterpenes and sesquiterpenes. In general, aromatherapy is a generic term that refers to any of the various traditions that make use of essential oils sometimes in combination with other alternative medical practices and spiritual beliefs. Popular use of these products include massaging products, medicine, or any topical application that incorporates the use of essential oils to their products. Essential oils are also commonly used in room diffuser products which typically include a container, such as a bottle, into which the essential oil is placed and a plurality of reeds which absorb the scent of the essential oils and then gently diffuse it throughout the room. One advantage of this product is that there are a wide array of essential oil products that can be used to create different, unique fragrances, from fruity fragrances, such as blood orange essential oil, to flowery fragrances, like lilac.

SUMMARY

An air freshener includes a housing having at least a first compartment and a second compartment, each of the first and second compartments having vents. The air freshener includes a first fan unit disposed within the first compartment and a second fan unit disposed within the second compartment. The air freshener also includes a first fragrance emitting substance disposed within the first compartment proximate the first fan unit and a second fragrance emitting substance disposed within the second compartment proximate the second fan unit. A programmable processor is operatively connected to a power source and the first and second fan units and configured to drive at least one of the first and second fan units so as to promote discharge of one of the fragrance emitting substances from the housing.

These and other aspects, features and advantages shall be apparent from the accompanying Drawings and description of certain embodiments of the invention.

BRIEF DESCRIPTION OF THE DRAWINGS

The present invention is illustrated by way of example and not by way of limitation in the figures of the accompanying drawings in which like references indicate similar elements.

DETAILED DESCRIPTION OF CERTAIN EMBODIMENTS OF THE INVENTION

Figure 1:
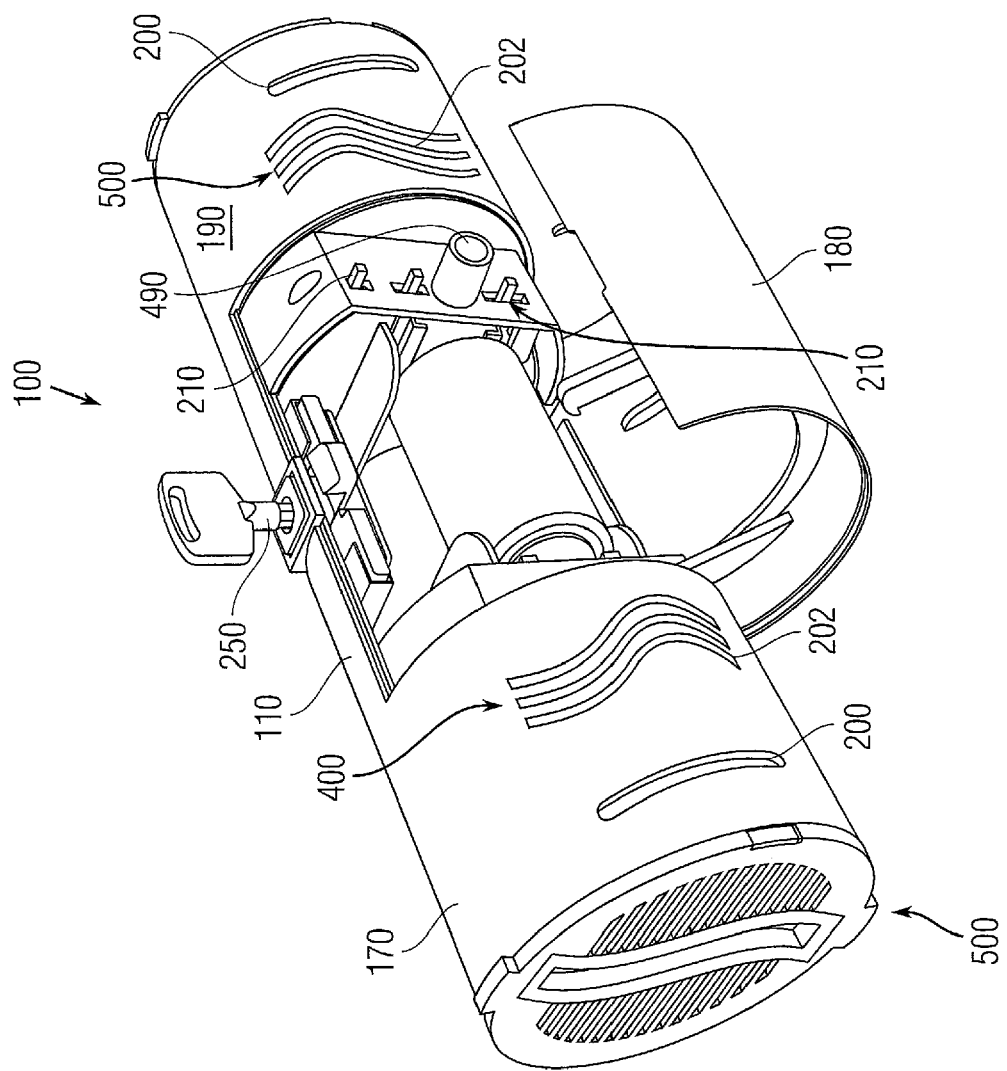
FIG. 1 is a front and end perspective view of a multi cartridge air freshener according to a first embodiment of the present invention in an open position.
Figure 2:
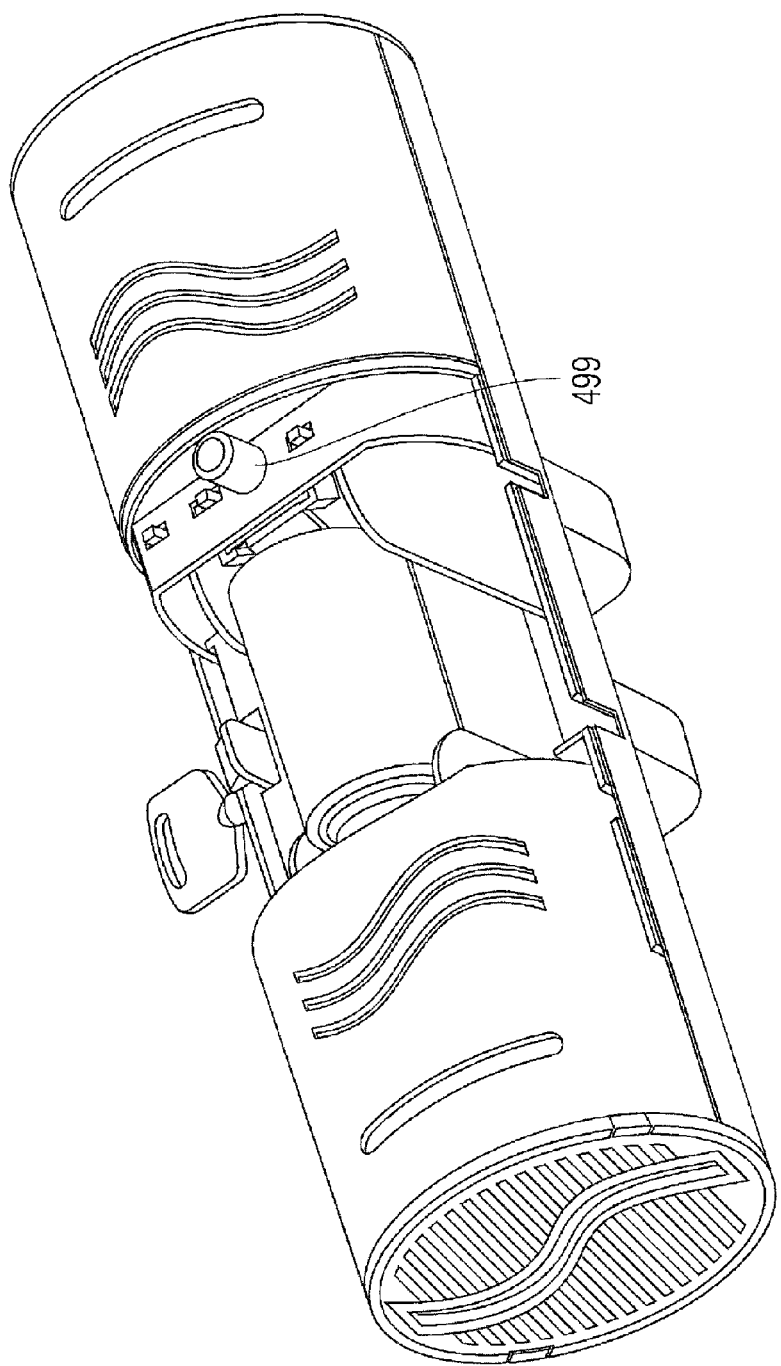
FIG. 2 is a front and end perspective view of the multi cartridge air freshener of FIG. 1 with a cover removed therefrom.
Figure 3:
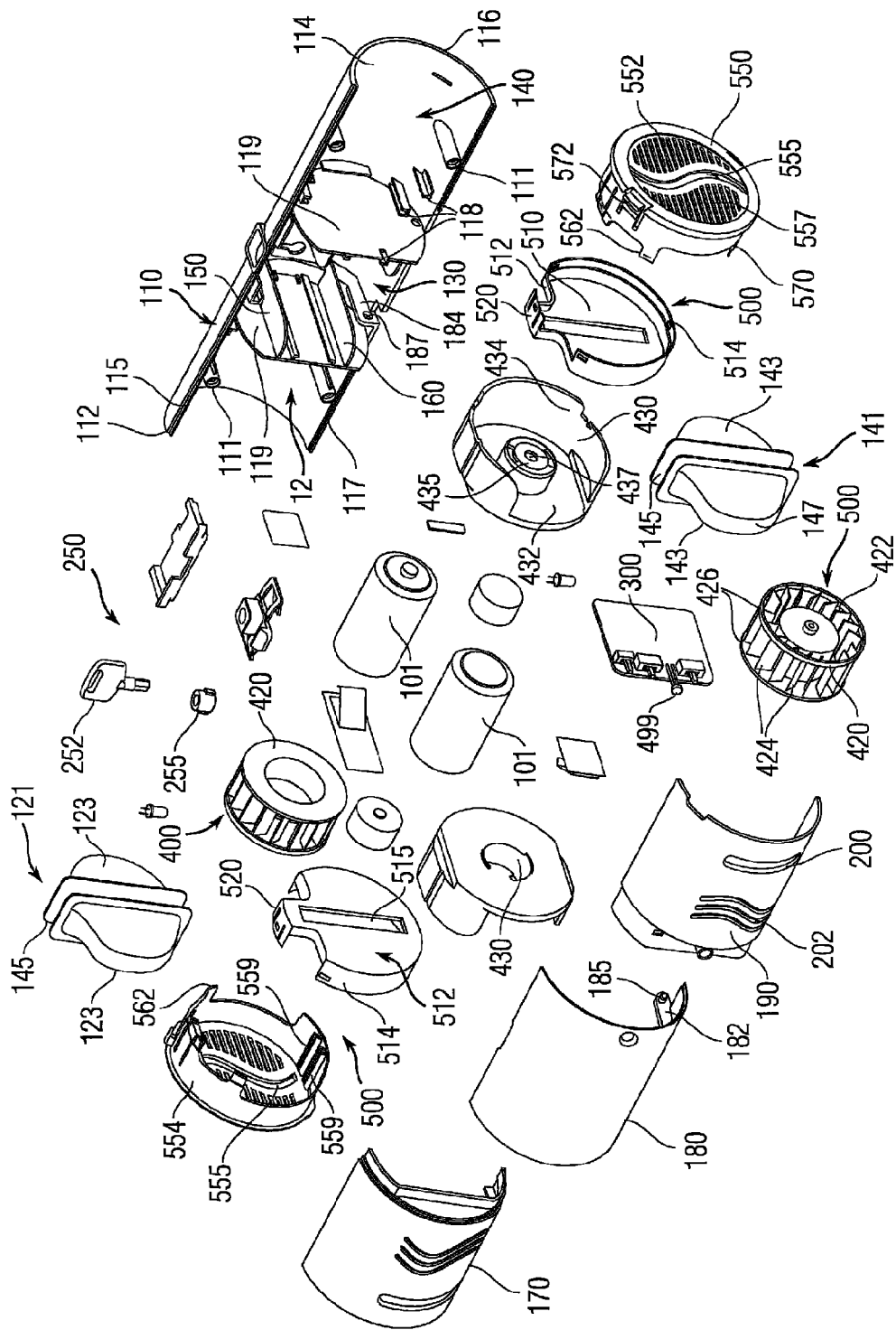
FIG. 3 is an exploded perspective view of the various components that make up the multi cartridge air freshener.
Figure 4:
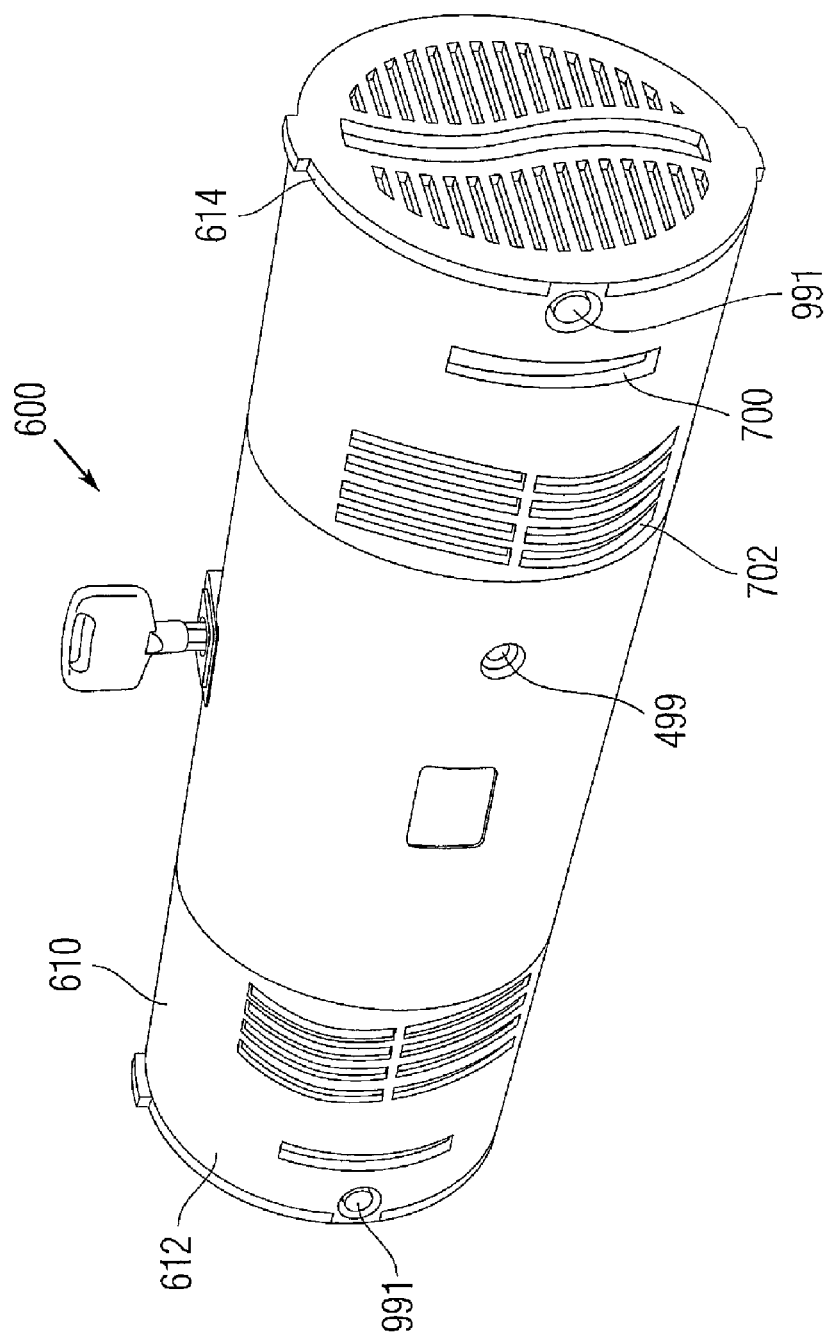
FIG. 4 is a front perspective view of a multi cartridge air freshener according to another embodiment.
Figure 5:
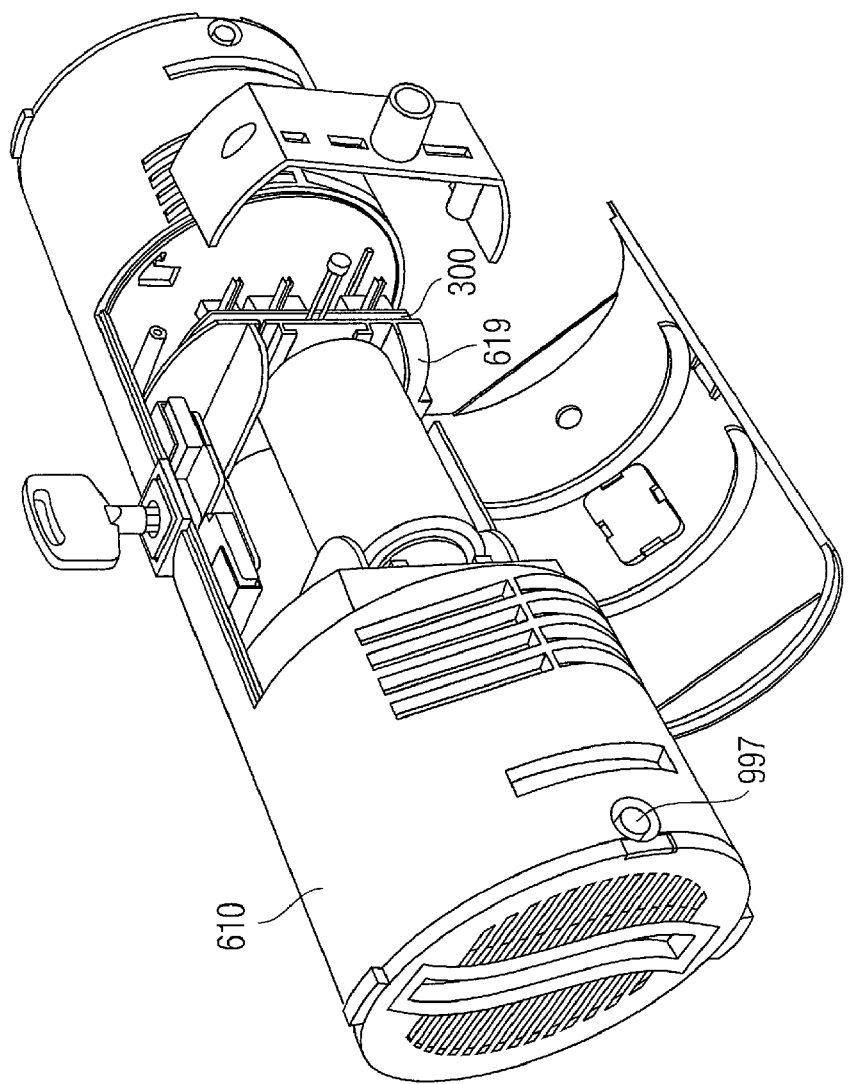
FIG. 5 is a partially exploded front perspective view of the air freshener of FIG. 4.
Figure 6:
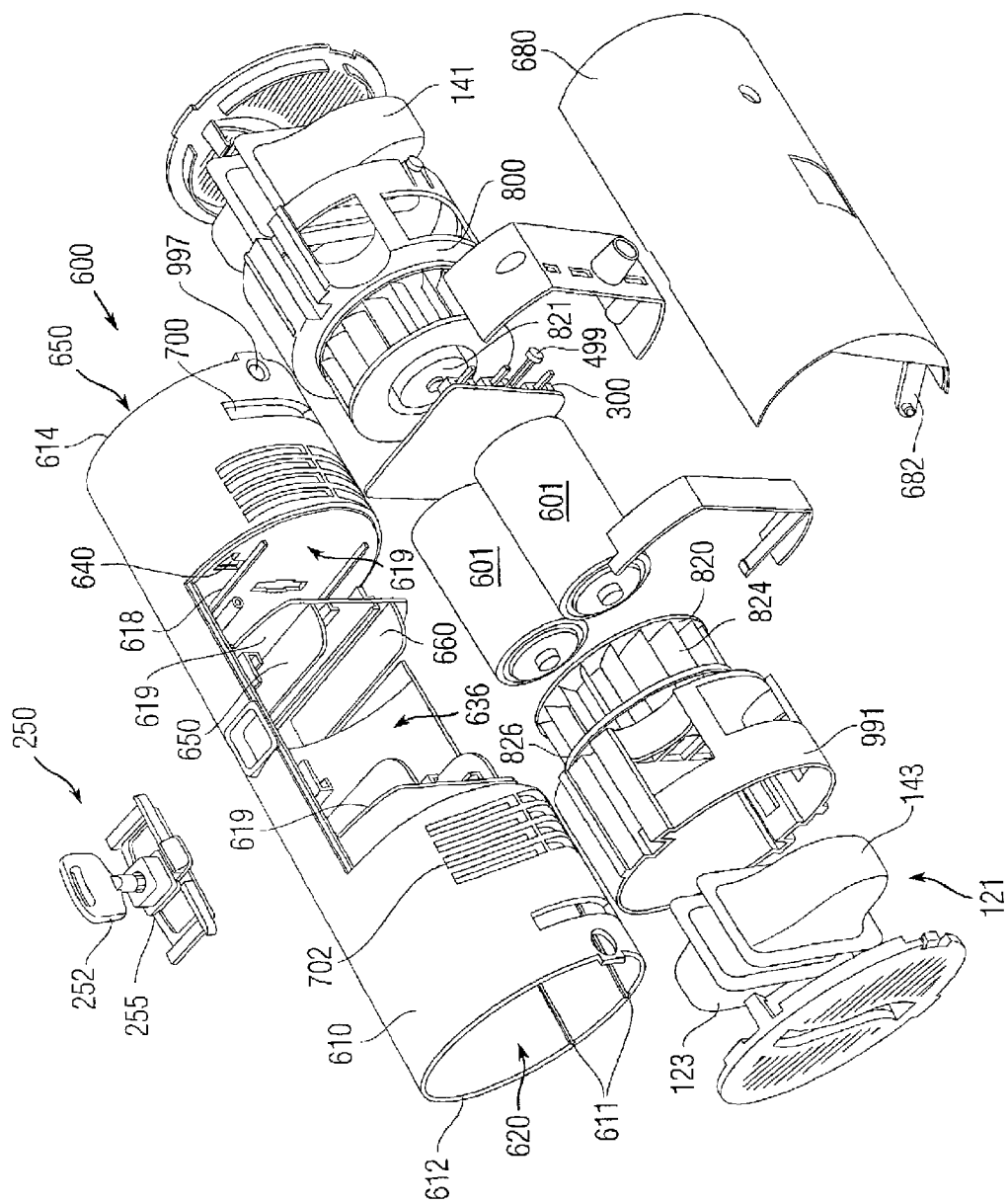
FIG. 6 is an exploded perspective view of the air freshener of FIG. 4.
Figure 7:
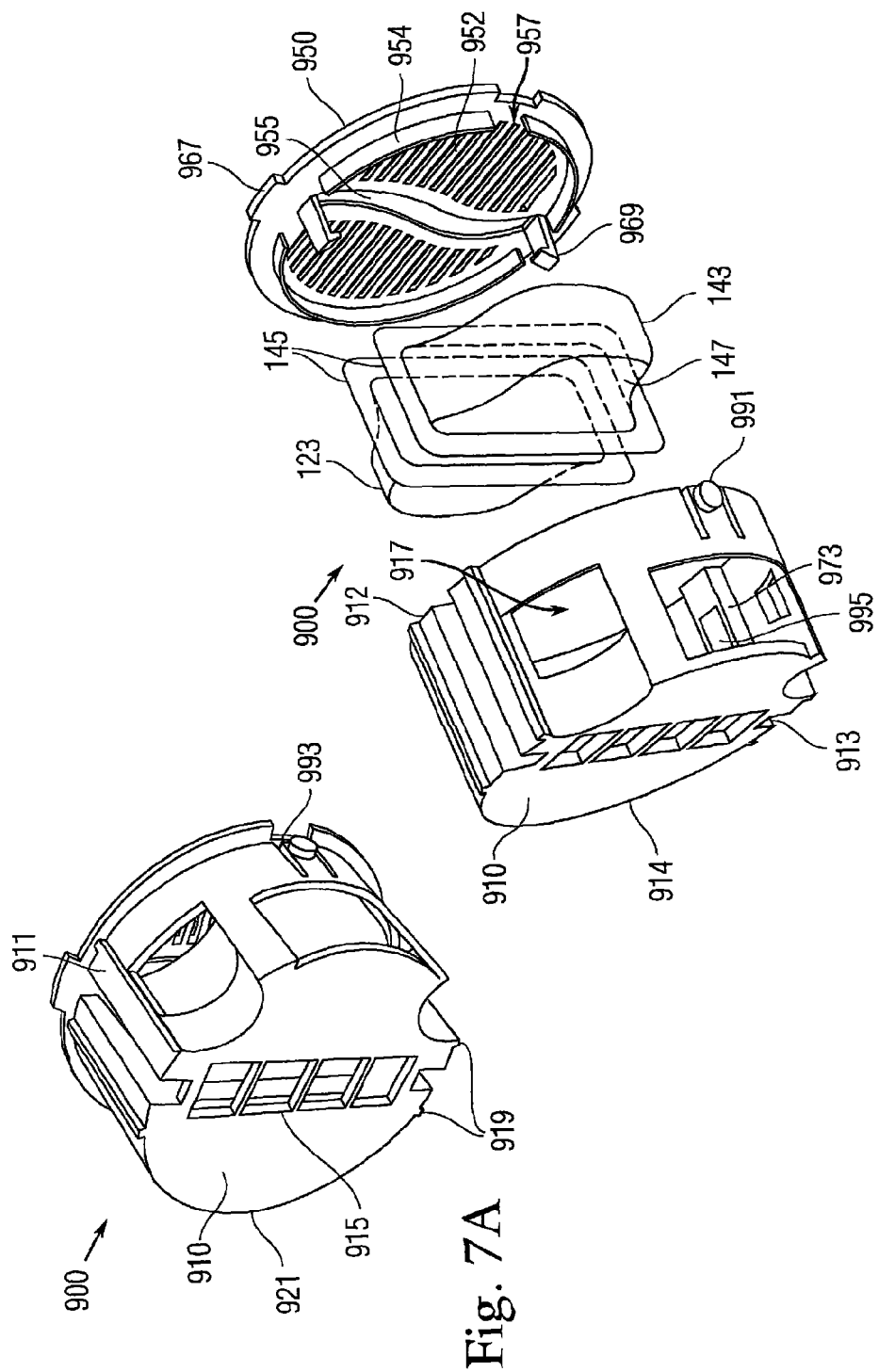
FIG. 7A is a perspective view of an assembled cartridge according to one embodiment.
FIG. 7B is an exploded perspective view of the cartridge of FIG. 7A.

FIGS. 1-3 illustrate a multi-cartridge air freshener 100 according to one embodiment of the present invention. The air freshener 100 includes a base 110 that has an arcuate shape and in particular has a semi-circular shape. The base 110 has an open first end 112 and an opposite open second end 114 and a curved rear surface 116. The base 110 can include a number of integral structural support members, such as ribs, 118 formed as a part thereof that serve not only to receive and support different members but also to partition the base 110 into different sections. For example, the base 110 can include a pair of vertical support walls 119 that extend between a top edge 115 of the base 110 and a bottom edge 117 of the base 110 and are spaced from one another so as to generally partition the base 110 into 3 sections or compartments, namely a first compartment 120, a second compartment 130 and a third compartment 140. The walls 119 can extend beyond the edges 115, 117 and can include first and second pairs of support tabs 150, 160. The support tabs 150, 160 are located within the second compartment 130 and face one another, with the pair of tabs 150 lying in one plane and the pair of tabs 160 lying in another plane. In other words, the tabs 150, 160 are formed along the inner surfaces of the vertical walls 120.

The air freshener 100 also includes a front housing which when assembled to the base 110 define a cylindrical shaped body that is open at its two ends. The front hosing includes a first or left cover panel 170, a second or center cover panel 180, and a third or right cover panel 190. Similar to the base 110, the three panels 170, 180, 190 have an arcuate shape in that they are curved structures (.e.g., semi-circular) that are open at both ends. It will be appreciated that each of the panels 170, 180, 190 can be detachably coupled to the base 110 using any number of different techniques, including but not limited to using fasteners. For example and as shown, the base 110 can include a number of threaded hollow bosses 111 and the panels 170, 180, 190 can include holes that align therewith and receive fasteners that securely attach the panels 170, 180, 190 separately to the base 110.

The left and right cover panels 170, 190 are designed to permit the fragrance to pass therethrough and therefore, each of the panels 170, 190 includes a number of openings to allow the emitted fragrance to pass therethrough. For example, each of the panels 170, 190 can include a first slot 200 that is constructed to allow the operator to view the level of fragrance left in a particular cartridge or container as discussed below and a plurality of other slots 202 through which the fragrance passes. The slots 202 can have an aesthetically pleasing look, such as waves or the like as shown. In the illustrated embodiment, there are three slots 202 formed side-by-side next to one another. The slots 200 are located closer to the ends 112, 114 of the base 110.

In accordance with the present invention, the air freshener 100 has dual functionality in that first compartment 120 stores a first fragrance source and the third component 140 stores a second fragrance source and each compartment 120, 140 includes independent working components that are configured to controllably emit a predetermined amount of fragrance at a select time as described in detail below. While the first and second fragrance sources can be the same, it is expected that the two will be different.

The center panel 180 does not include air flow slots, such as slots 202, since this section houses electronic components and a power source, as described below, and does not include a fragrance source. The center panel 180 is designed to be opened and closed relative to the base 110 and therefore, the center panel 180 can be coupled to the base 110 in a number of different ways. For example, the center panel 180 can be pivotally coupled to the base 110. In the illustrated embodiment, the center panel 180 has an arm 182 that is coupled to a center tab 184 of the base 110 in a pivotal manner (e.g., a pin 185 at the end of the arm 182 is inserted into an opening 187 formed in the arm 182. The center panel 180 thus pivots at its bottom and opens in a top to bottom manner to expose the second interior compartment 130.

The second interior compartment 130 houses a number of working components of the air freshener 100 including a power source 101. The power source 101 can be in the form of one or more batteries 200 that can be easily removed and replaced by simply opening the center panel 180. A lock mechanism 250 including a key 252 can be provided for securely locking the center panel 180 relative to the base 110. The lock mechanism 250 can include a lock component 255 into which the key 252 is inserted and the lock component 255 has a tabs that extend radially outwardly therefrom such that rotation of the lock component 255 causes engagement or disengagement of the tabs with other components, resulting in either the center panel 180 being locked or unlocked, respectively.

Since each of the compartments 120, 140 houses its own fragrance source, each of the compartments 120, 140 has a mechanism for controllably causing the release of the fragrance. For example, a first mechanism 400 is disposed within the first compartment 120 for controllably and selectively releasing a quantity of a first fragrance emitting substance, while a separate second mechanism 500 is disposed within the third compartment 140 for controllably and selectively releasing a quantity of a second fragrance emitting substance. In the illustrated embodiment, the each of the first and second mechanisms 400, 500 includes a controllably fan that is formed of a rotatable fan blade unit 420 and a housing 430 for containing the fan blade unit 420. The fan is operatively connected to a processor (circuit board/microchip) 300 is also disposed within center compartment 130 and is connected to and powered by the power source 101. User accessible controls 210 and indicator lights (not shown) can also be contained within the center compartment 130 and accessible when the center panel or door 180 is opened. For example, the controls 210 can include any number of different operating states or conditions, such as fan speed (Hi or Low), fragrance release or cycle time period, such as one hour, three hours or six hours, and different operating modes, such as 24 hour mode (constant operation), night mode where the unit only operates at set times occurring during the night, and day mode where the unit only operates at set times occurring during the day.

The fan blade unit 420 includes a center drive portion 422 and a number of blades 424 in the form of blades or baffles or the like, as shown. The blades 424 are arranged circumferentially around the center drive portion 422 and are attached at their ends to circular support structures 426. The housing 430 has an inner end wall 432 and a flange 434 that extends radially outward from the end wall 432 and at least partially encloses the end wall 432. The flange 434 extends circumferentially about a peripheral edge of the inner end wall 432. The inner diameter of the flange 434 is selected so that the fan blade unit 420 can be fully contained therein. On an outwardly facing surface 433 of the end wall 432, a hub 435 or the like is formed with a central opening 437 formed therethrough. The opening 437 can receive a drive component, such as a drive shaft, etc., that is operatively coupled to the fan blade unit 420 such that rotation thereof is translated into rotation of the fan blade unit 420. Other techniques can be used to rotate the fan blade unit 420 at one or more speeds to create air movement. The fan blade unit 420 thus faces one end of the assembled dispenser 100. Any number of different means, including creating a mechanical fit, can be used to couple the 410 (e.g., housing 430 thereof) to the base 110. For example, a snap-fit can be formed between the two parts. The vertical support wall 119 can be used a surface to which the housing 430 is coupled.

When the fan is installed within its respective first or third compartment 120, 140, the fan blade unit 420 thereof is aligned with the air flow slots 202 that are formed in the respective left and right cover panels 170, 190. This positioning allows the emitted fragrance to be more effectively directed through the slots 202 and out of the air freshener 100 into the room. Since the air freshener 100 has dual operation capability, each fragrance source has its own fan 410 and each is controlled independently via the processor (circuit board) 300. As can be seen in the drawings, this functionality and arrangement of parts provides a degree of symmetry in that the left side is symmetric to the right side of the air freshener 100.

The air freshener 100 also includes a holder 500 for containing the fragrant emitting substance. For example, the holder 500 can include a base plate 510 that is constructed to be received within the base 110. The base plate 510 has a first wall 512 and a side wall 514 that extends around a periphery of the wall 512 and extends outwardly therefrom. The first wall 512 has a slot 515 formed therein. The illustrated slot 515 is rectangular in shape and when the base plate 510 is installed in the base 110, the slot 515 is oriented vertically. The side wall 514 does not extend completely around the periphery but instead is absent along a top section of the base plate 510. The wall 512 and side wall 514 thus define an interior compartment 517. The top section of the base plate 510 includes a coupling member (bracket like member) 520 that is used to couple the holder 500 to the base 110. The coupling member 520 is axially aligned with the vertical slot 515. The curved side wall 514 of the base plate 510 complements and seats against the curved surface of both the base 110 and one of the left or right cover panels 170, 190. When installed, the base plate 510 stands vertically in the base 110 and the curved side walls of the base plate 510 and the base 110 abut one another.

The interior compartment 517 is constructed to at least partially receive one or more fragrance sources. As previously mentioned, the first compartment 120 stores a first fragrance source 121 and in particular, the first fragrance source 121 is contained within the holder 500 that is disposed in the first compartment 120. Similarly, the second compartment 140 stores a second fragrance source 141 and in particular, the second fragrance source 141 is contained within the holder 500 that is disposed in the second compartment 140.

For example and as shown, the each of the fragrance sources 121, 141 can include a pair of cartridges 123, 143, respectively. Each cartridge 123, 143 includes a hollow shell that has a first wall or face 145 that can be a planar surface and a sloped curved body portion 147 that defines the interior compartment in which an essential oil fragrance is stored. When a pair cartridges 123, 143 are used, the two walls 145 of the two cartridges 123, 143 face one another with the curved body portions 147 facing in opposite directions. When combined, the two cartridges of one pair define a generally circular structure that is sized to be received and contained in the holder 500. When the pair of cartridges are inserted into the holder 500, the two walls 145 align with the slot 515.

The core of the fragrance that is contained in the cartridge 123, 143 is one or more essential oils. Incorporating natural essential oils into the fragrance provides a number of advantages compared to chemical based fragrances. Not only will the room be fragranced by pure natural oils extracted from a botanical material, but occupants of the room will also benefit from the therapeutic effects intrinsic to the oils. There are literally hundreds of oils to choose from, and therefore, the room does not have to smell like one that has been masked with traditional commercial air freshener fragrances. Since the base of the fragrance is an essential oil, it is vegan friendly, environmentally safe and biodegradable.

It will be appreciated that the cartridge 123, 143 can be a shell-like container that holds liquid essential oils and the air freshener can have some type of releasing mechanism for releasing controlled quantities of the essential oils. For example, the cartridge 123, 143 can be a hollow container that stores the essential oil, which is in liquid form. The cartridge 123, 143 can include a membrane, such as a semi-permeable membrane, that has one surface in contact with the essential oil and has another surface that is covered with a protective sheet or cover until use. When the cartridge 123, 143 is loaded into the holder 500, the protective sheet is removed, thereby exposing the membrane to ambient conditions within the interior of the air freshener 100. The membrane is designed so that the essential oil passes through the membrane by diffusion and enters the interior of the holder 500 as a gas. It will be appreciated that there can be a plurality of membranes, such as when the cartridge shell includes a plurality of holes each of which is covered with a membrane and a protective sheet. The concentration of the essential oil thus increases in the interior of the holder 500 compared to the exterior of the air freshener 100. The operation of the fan unit, thus creates air turbulence and air streams that forces the concentrated essential oil gas out of the interior of the holder 500 and into the room surrounding the air freshener 100. The fan unit thus disperses the essential oil gas through the room. The cartridge will need replacement once all of the essential oil diffuses out of the cartridge.

It will be appreciated that other techniques can be employed to introduce the essential oil in gas form to the fan unit. For example, the cartridge can be a container that includes a valve, e.g., a drip valve, that releases a small quantity of the essential oil to a warmer (heating element (e.g., a filament)) that serves to heat and vaporize the essential oil, whereby the action of the fan causes the heated, evaporated fragrance to be expelled from the air freshener 100 and into the room. In other words, the air freshener 100 operates by injecting a small amount of the essential oil into the oil warmer unit which causes the oil to evaporate and the proximity to the fan unit 410 results in the essential oil fragrance being emitted through the slots 202 and into the room. Operation of the heating element and the fan unit can be coordinated with one another so that the fan unit operates right after operation of the heating element. Alternatively, the fragrance emitting substance can be a solid structure, such as a gel that contains essential oils. The action of the fan causes the fragrance to be emitted from the air freshener 100 and travel within the room.

The holder 500 includes a cover 550 that is designed to mate with the base plate 510. The cover 550 includes an end wall 552 and a side wall or flange 554 that extends at least partially and preferably circumferentially around a peripheral edge of the end wall 552. The end wall 552 thus has a circular shape. The end wall 552 is not a completely solid structure but instead has a number of air flow slots, e.g., a first type of slot 555 and a second type of slot 557. The slot 555 can be in the form of a generally up-and-down oriented slot, while the slots 557 are left-to-right slots. The slots 557 are thus arranged so that they are perpendicular to the slot 555. The cover 550 is thus designed to allow the essential oil fragrance to flow out of the ends of the air freshener 100. The walls 512, 552 are thus parallel to one another when the holder 500 is assembled.

The cover 550 also has a number of locating and retention members for locating and retaining the cartridge 123, 143 in place within the holder 500 and relative to one another. For example, an inner surface of the side wall 554 can include two pairs of opposing slotted rails 559. The rails 559 are formed in an enlarged section of the side wall 554. Each pair of slotted rails 559 is located opposite one another (e.g., 180 degrees apart) and is designed to capture and hold one cartridge 123, 143. The rail 559 is an elongated structure (e.g., rectangular cross-section) with a slot formed therein that extends along its length and is open at one end to permit insertion of an object. The spacing between the pairs of rails 559 is designed to allow the pair of cartridges 123, 143 to be inserted and captured within the cover 550 in a spaced, facing relationship. For example, the width of the slot in the rail 559 is selected so that the wall 145 of one cartridge can be inserted therein. The pair of opposite rails 559 are formed so that the opposite ends 145 of the cartridge can be disposed within the slots of the opposite rails 559 and thereby, held in place within the cover 550. When the two cartridges 123, 143 are inserted into the respective slots of the rails 559, the two cartridges 123, 143 are securely held in place therein with the appropriate amount of spacing between the exposed membranes of each cartridge 123, 143 to permit diffusion of the essential oil. The rails 559 thus permit easy insertion, retention and removal of the cartridges 123, 143.

The cover 550 can be coupled to the base plate 510 using any number of different techniques, including mechanical coupling members including snap-fit coupling members. For example, the side wall 514 near the coupling member 520, can include a pair of slots 560 and the cover 550 can include complementary locking tabs 562 that are received into the slots 560 resulting in a mechanical fit between the cover 550 and the base plate 510.

Similarly, the assembled holder 500 is coupled to the air freshener 100 using conventional techniques. For example, the cover 550 can include a locking tab 570 that is a resilient tab structure that can flex and includes a locking ridge or the like. When the holder 500 is inserted into the assembled base and front cover structure, the flange 554 fits between the assembled base and front cover structure due to its complementary shape. Continued insertion of the holder 500 into the assembled base and front cover structure causes the locking tab 570 to flex downward until a lip 572 at the end of the locking tab 570 clears one end of the air freshener 100 resulting in the lip 572 flexing upward. This results in a mechanical coupling (e.g., snap-fit) between the holder 500 and the assembled air freshener body; however, the holder 500 can easily be disengaged and removed by simply pressing down on the lip 572 and then pulling the holder 500 out of the air freshener. The holder 500 is ordinarily taken out of the air freshener 100 when replacement of the essential oil substances is needed. In addition, the holder 500 includes vent slots as well as the front cover and therefore, the essential oil fragrance is emitted both from the ends of the air freshener 100 but also from the front cover as well. This provides a better distribution of the essential oil fragrance throughout the room.

As previously mentioned, the air freshener 100 can include a number of different controls and operating modes and can include one or more sensors, e.g., 499. Sensor 499 can be of the type that the air freshener 100 is turned on automatically when the room gets dark and off when the room gets light. Other sensors can likewise be used. In accordance with the present invention, the air freshener 100 offers independent dual functionality where two different fragrances can be emitted in a controlled manner. In other words, since there are two independently operated fan units, two fragrances can be emitted at different, select times based on user inputted instructions or based on a program. For example, a program can be configured to have one fragrance, such as a citrus based essential oil, be emitted during the morning hours, while in the afternoon, a second fragrance is emitted. The time period over which each fragrance is emitted is also based on user input. For example, first fragrance can be emitted over a time period of 1, 2, 3, 4 hours, etc., and then the second fragrance is emitted over a time period of 1, 2, 3, 4 hours, etc. In most operating states, the first and second fragrances are not emitted at the same time but instead, the two fragrances are emitted successively over a period of time. For example, the first fragrance can be emitted for 3 hours and then the second fragrance is emitted for 3 hours. This process can be repeated over the day.

It will be appreciated that the processor can be controlled by a program that allows the user to set the operating parameters in that the air freshener can only operate during normal or extended business hours in the case of the air freshener being installed in a corporate building, such as in a bathroom or in a lobby. When the air freshener is installed in a person's house, the air freshener can be constructed so that during the overnight hours, the air freshener does not operate.

The air freshener 100 is also designed to incorporate a degree of symmetry in that the two ends of the air freshener 100 through which the fragrances are emitted have the same appearance as one another. This symmetry also results due to the inclusion of two separate fan units to discharge the essential oil fragrances. It will also be appreciated that the two fragrances can be complementary to one another in that one fragrance can be emitted as a base fragrance and then the second fragrance can be emitted to add some simple complexity to the fragrance. For example, the base essential oil can be in the form of a citrus flavor (essential oil), and the second fragrance can be another citrus flavor or a flower fragrance that adds complexity (adds a flowery note) to the base citrus fragrance.

Since there are so many essential oil substances available, the operator can select from many different essential oil combinations and since the air freshener 100 is a cartridge based system, the user can simply change one essential oil fragrance for another. Unlike traditional air fresheners that only offer a single fragrance smell, the present air freshener provides a dual fragrance experience and allows a user customization that is not available with traditional air fresheners.

The components that make up the air freshener 100 can be formed of a plastic material or other suitable material.

In yet another aspect of the present invention, instead of the holders 500 containing cartridges that hold essential oils (fragrance), the device 100 can be configured to act has an insecticide (pest) repellant. More specifically, each holder (refill casing) 500 includes two cartridges, namely, cartridges 123, 143, the cartridge 123 can contain a pesticide (insecticide), while the cartridge 143 includes a fragrance or vice versa. The pesticide can be a liquid formulation that is contained in its own cartridge similar to how the essential oil is contained in the other cartridge. It will also be appreciated that the pesticide can even be a solid material, such as a gel, so long as the pesticide properly diffuses (osmosis) from the cartridge.

As is well known, the problem with pest repellants is that they have a strong, unappealing smell that is very difficult to mask. While commercial pesticides attempt to mask the unappealing smell by combining a fragrance with the pesticide, the fragrance does not mask the pesticide smell. In addition, there are guidelines from the EPA that govern such products and the inclusion of a fragrance in the product affects the formulation and requires heavy amendments to the labeled formula.

The present invention avoids the aforementioned problem and limitations associated with the conventional commercial products. More specifically, the cartridge 123, 143 that contains the fragrance masks the unappealing smell of the pesticide that is contained in the other cartridge 143, 123, while the pesticide is effectively dispersed under action of the fan, etc. In addition, since the holder 500 can easily be removed and replaced, the type of pesticide can be easily changed depending upon the condition that needs to be treated (e.g., if the device is used outdoors, a mosquito repellant could be used as the pesticide). It will further be appreciated that the in the event that the pesticide problem has been rectified, the user can simply remove the pesticide containing cartridge and insert another fragrance cartridge (essential oil) as in the first embodiment described herein. Accordingly, the present invention offers great flexibility and effectiveness in providing a pleasant smelling pesticide product.

FIGS. 4-8 illustrate a multi-cartridge air freshener 600 according to another embodiment. The air freshener 600 is similar to the air freshener 100 shown in FIGS. 1-3. The air freshener 600 includes a base 610 that generally has a cylindrical shape and is formed as a single molded structure. The base 610 has an open first end 612 and an opposing open second end 614. The base 610 includes a number of integral structural support members, such as ribs 618 that are formed as part of the base 610 and serve not only to receive and support different members also serve to partition the base 610 into different sections. For example, the base 610 can include three vertical support walls 619 that extend between a top of the base 610 and a bottom of the base 610. The vertical support walls 619 generally partition the base 610 into four compartments, namely, a first compartment 620, a second compartment 630, a third compartment 640 and a fourth compartment 650. Two of the vertical support walls 619 can include first and second pairs of support tabs 659, 660. The support tabs 659, 660 are located within the second compartment 630 and face one another, with the pair of tabs 650 lying in one plane and the pair of tabs 660 lying in another plane. In other words, the tabs 659 and 660 are formed along the inner surfaces of the vertical walls.

The air freshener 600 also includes a front housing which when assembled to the base 610 define a cylindrical shaped body that is open at its two ends. The front hosing includes a center cover panel 680 and unlike the first embodiment, the front housing of freshener 600 does not include left and right covers 170 and 190 (FIG. 3) but instead these two fan covers have been incorporated into the base 610. Similar to and to complement the base 610, the panel 680 has an arcuate shape in that it is a curved structure (.e.g., semi-circular). The panel 680 can be detachably coupled to the base 610 using any number of different techniques, including but not limited to using fasteners or a pivot connection.

In the present embodiment, the left and right front portions 670, 690 of the base 610 are part of the base 610 and are designed to permit the fragrance to pass therethrough and therefore, each of the portions 670, 690 includes a number of openings to allow the emitted fragrance to pass therethrough. For example, each of the portions 670, 690 can include a first slot 700 that is constructed to allow the operator to view the level of fragrance left in a particular cartridge or container as discussed below and a plurality of other slots 702 through which the fragrance passes. The slots 702 can have an aesthetically pleasing look, such as waves or the like as shown. In the illustrated embodiment, there are four slots 702 formed side-by-side next to one another. The slots 700 are located closer to the ends 612, 614 of the base 610.

In accordance with the present invention, the air freshener 600 has dual functionality in that first compartment 620 stores a first fragrance source and the fourth component 650 stores a second fragrance source and each compartment 620, 650 includes independent working components that are configured to controllably emit a predetermined amount of fragrance at a select time as described in detail below. While the first and second fragrance sources can be the same, it is expected that the two will be different.

The center panel 680 does not include air flow slots since this section houses electronic components and a power source, as described below, and does not include a fragrance source. The center panel 680 is designed to be opened and closed relative to the base 610 and therefore, the center panel 680 can be coupled to the base 610 in a number of different ways. For example, the center panel 680 can be pivotally coupled to the base 610. In the illustrated embodiment, the center panel 680 has an arm 682 that is coupled to a center tab of the base 610 in a pivotal manner. The center panel 680 thus pivots at its bottom and opens in a top to bottom manner to expose the second interior compartment 630.

The second interior compartment 630 houses a number of working components of the air freshener 600 including a power source 601. The power source 601 can be in the form of one or more batteries that can be easily removed and replaced by simply opening the center panel 680. A lock mechanism 250 including a key 252 can be provided for securely locking the center panel 680 relative to the base 110. The lock mechanism 250 can include a lock component 255 into which the key 252 is inserted and the lock component 255 has a tabs that extend radially outwardly therefrom such that rotation of the lock component 255 causes engagement or disengagement of the tabs with other components, resulting in either the center panel 680 being locked or unlocked, respectively.

Since each of the compartments 620, 650 houses its own fragrance source, each of the compartments 620, 650 has a mechanism for controllably causing the release of the fragrance. For example, a first mechanism 700 is disposed within the first compartment 620 for controllably and selectively releasing a quantity of a first fragrance emitting substance, while a separate second mechanism 800 is disposed within the fourth compartment 650 for controllably and selectively releasing a quantity of a second fragrance emitting substance. In the illustrated embodiment, the each of the first and second mechanisms 700, 800 includes a controllably fan that is formed of a rotatable fan blade unit 820. In the illustrated embodiment, the fan unit 700 is disposed within the first compartment 620 along an outer face of the vertical wall that separates the first compartment 620 from the second compartment 630 and similarly, the fan unit 800 is disposed within the fourth compartment 650 along an outer face of the vertical wall that separates the third compartment 640 from the fourth compartment 650. The vertical walls can include openings that permit drive shafts and other drive components, such as bearings, to pass through.

The fan is operatively connected to a processor (circuit board/microchip) 300 is also disposed within center compartment 630 and is connected to and powered by the power source 101. User accessible controls 210 (see FIG. 1) and indicator lights (not shown) can also be contained within the center compartment 630 and accessible when the center panel or door 680 is opened. For example, the controls 210 can include any number of different operating states or conditions, such as fan speed (Hi or Low), fragrance release or cycle time period, such as one hour, three hours or six hours, and different operating modes, such as 24 hour mode (constant operation), night mode where the unit only operates at set times occurring during the night, and day mode where the unit only operates at set times occurring during the day.

Figure 8:
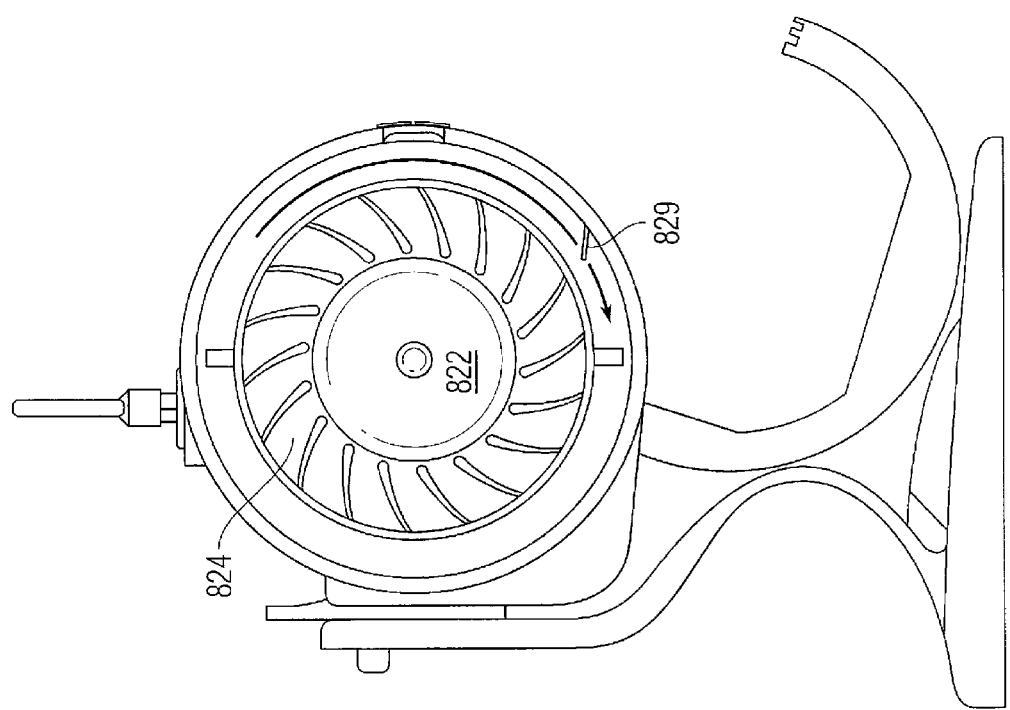
FIG. 8 is an end view showing the blade of the fan assembly.

The fan blade unit 820 includes a center drive portion 822 and a number of blades 824 in the form of blades or baffles or the like, as shown. The blades 824 are arranged circumferentially around the center drive portion 822 and are attached at their ends to circular support structures 826. The fan blade unit 820 is operatively coupled to working fan components, such as a hub 821, that can receive a drive component, such as a drive shaft, etc., to permits the drive shaft to be operatively coupled to the fan blade unit 820 such that rotation thereof is translated into rotation of the fan blade unit 820. Other techniques can be used to rotate the fan blade unit 820 at one or more speeds to create air movement. The fan blade unit 820 thus faces one end of the assembled dispenser 100. As shown in FIG. 8, the blades 824 of the two different fan blade units 820 are oriented in different directions. For example, FIG. 8 shows the left end (first end 612) of the air freshener 600 and the blades 824 at this end are oriented in a clockwise direction. Conversely, the blades 824 of the fan blade unit 820 that is located at the other end (right end/second end 614) of the air freshener 600 are oriented in a counter clockwise direction.

In yet another aspect of the present invention, an air deflector 829 is provided for improving air flow around the fan unit 820 and more particularly, for forcing air to exit the air freshener 600 through the respective air vents. As shown in FIG. 9 at each end of the base 610, one air deflector 829 in the form of a lip or fin is provided and extends radially inward from the inner surface of the base 610; however, the air deflector 829 does not interfere with the rotation or operation of the fan unit 820. The air deflector 829 is located below the air vents 202 formed in the base 610 and is locate near the bottom of the base 610. As the fan unit 610 operates air can in effect stick to the blades and this results in the air not properly being vented from the air freshener and therefore, the emission of the fragrance is likewise not optimized. The air deflector 829 is thus strategically located that it acts to deflect and force more air off the blades 824 and through the air vents 202. The air deflector 829 is set at an angle to cause air that causes some turbulence to occur or otherwise redirects air from the blades back toward the vents 202.

When the fan is installed within its respective first or fourth compartment 620, 640, the fan blade unit 820 thereof is aligned with the air flow slots 202 that are formed in the respective left and right portions 670, 690 of the base 610. This positioning allows the emitted fragrance to be more effectively directed through the slots 202 and out of the air freshener 600 into the room. Since the air freshener 600 has dual operation capability, each fragrance source has its own fan 410 and each is controlled independently via the processor (circuit board) 300. As can be seen in the drawings, this functionality and arrangement of parts provides a degree of symmetry in that the left side is symmetric to the right side of the air freshener 100.

The air freshener 600 also includes a holder 900 for containing the fragrant emitting substance. For example, the holder 900 can include a housing 910 that is constructed to be received within the base 610. FIG. 7a shows the holder 900 in an assembled condition, while FIG. 7b shows the individual components of the holder 900 in an exploded (nonasembled condition).

The housing 910 is a hollow generally cylindrical shell that has an open first end 912 and an at least partially open second end 914 and a rear surface 921 at end 914. The housing 910 has a top portion 911 and a bottom portion 913 when the housing 910 is placed in a vertical position. The side of the housing 910 includes openings that permit the interior of the housing 910 to be seen. The rear surface 921 faces inwardly toward the center of the base 610 when the holder 900 is vertically disposed within its respective compartment. The rear surface 921 includes a slot 915 (e.g., a vertically oriented slot when the holder 900 is disposed vertically in the base 610). Along the bottom portion 913 when the housing 910 is positioned vertically, a pair of guide rails 919 (a guide feature) is formed and is spaced apart from one another. The guide rails 919 are complementary to a pair of grooves or channels 611 (a guide feature) formed along the inner surface of the bottom of the base 610. To properly locate and couple the assembled holder 900 with the base 610, the guide rails 919 are inserted into the grooves 611, thereby coupling the holder 900 to the base 610. The leading grooves 611 extend completely to the respective open end of the base 610 and therefore make it easier for a user to both load and remove the cartridge holder 900. It will be appreciated that the opposite arrangement is equally possible in that the guide rails 919 can be formed along a bottom of the base 610 and the grooves 611 can be formed along the bottom portion 913 of the housing 910.

Along an outer surface of the housing 910, a release button 991 is formed and serves to permit the holder 900 to be easily disengaged and removed from the base 610 as described below.

When installed, the housing 910 stands vertically within the interior of the base 610 and the curved side walls of the housing 910 and the curved inner surface of the base 610 abut one another.

The housing 910 defines an interior compartment 917 is constructed to at least partially receive one or more fragrance sources. As previously mentioned, the first compartment 620 stores a first fragrance source 121 and in particular, the first fragrance source 121 is contained within the holder 900 that is disposed in the first compartment 120. Similarly, the fourth compartment 650 stores a second fragrance source 141 and in particular, the second fragrance source 141 is contained within the holder 900 that is disposed in the fourth compartment 650.

For example and as shown, the each of the fragrance sources 121, 141 can include a pair of cartridges 123, 143, respectively. Each cartridge 123, 143 includes a hollow shell that has a first wall or face 145 that can be a planar surface and a sloped curved body portion 147 that defines the interior compartment in which an essential oil fragrance is stored. When a pair cartridges 123, 143 are used, the two walls 145 of the two cartridges 123, 143 face one another with the curved body portions 147 facing in opposite directions. When combined, the two cartridges of one pair define a generally circular structure that is sized to be received and contained in the holder 500. When the pair of cartridges are inserted into the holder 500, the two walls 145 align with the slot 915.

The core of the fragrance that is contained in the cartridge 123, 143 is one or more essential oils. Incorporating natural essential oils into the fragrance provides a number of advantages compared to chemical based fragrances. Not only will the room be fragranced by pure natural oils extracted from a botanical material, but occupants of the room will also benefit from the therapeutic effects intrinsic to the oils. There are literally hundreds of oils to choose from, and therefore, the room does not have to smell like one that has been masked with traditional commercial air freshener fragrances. Since the base of the fragrance is an essential oil, it is vegan friendly, environmentally safe and biodegradable.

It will be appreciated that the cartridge 123, 143 can be a shell-like container that holds liquid essential oils and the air freshener can have some type of releasing mechanism for releasing controlled quantities of the essential oils. For example, the cartridge 123, 143 can be a hollow container that stores the essential oil, which is in liquid form. The cartridge 123, 143 can include a membrane, such as a semi-permeable membrane, that has one surface in contact with the essential oil and has another surface that is covered with a protective sheet or cover until use. When the cartridge 123, 143 is loaded into the holder 900, the protective sheet is removed, thereby exposing the membrane to ambient conditions within the interior of the air freshener 100. The membrane is designed so that the essential oil passes through the membrane by diffusion and enters the interior of the holder 900 as a gas. It will be appreciated that there can be a plurality of membranes, such as when the cartridge shell includes a plurality of holes each of which is covered with a membrane and a protective sheet. The concentration of the essential oil thus increases in the interior of the holder 900 compared to the exterior of the air freshener 600. The operation of the fan unit, thus creates air turbulence and air streams that forces the concentrated essential oil gas out of the interior of the holder 900 and into the room surrounding the air freshener 600. The fan unit thus disperses the essential oil gas through the room. The cartridge will need replacement once all of the essential oil diffuses out of the cartridge.

It will be appreciated that other techniques can be employed to introduce the essential oil in gas form to the fan unit. For example, the cartridge can be a container that includes a valve, e.g., a drip valve, that releases a small quantity of the essential oil to a warmer (heating element (e.g., a filament)) that serves to heat and vaporize the essential oil, whereby the action of the fan causes the heated, evaporated fragrance to be expelled from the air freshener 600 and into the room. In other words, the air freshener 600 operates by injecting a small amount of the essential oil into the oil warmer unit which causes the oil to evaporate and the proximity to the fan unit results in the essential oil fragrance being emitted through the slots 202 and into the room. Operation of the heating element and the fan unit can be coordinated with one another so that the fan unit operates right after operation of the heating element. Alternatively, the fragrance emitting substance can be a solid structure, such as a gel that contains essential oils. The action of the fan causes the fragrance to be emitted from the air freshener 600 and travel within the room.

The holder 900 includes a cover 950 that is designed to mate with the housing 910. The cover 950 includes an end wall 952 and a side wall or flange 954 that extends at least partially and preferably circumferentially around a peripheral edge of the end wall 952. The end wall 952 thus has a circular shape. The end wall 952 is not a completely solid structure but instead has a number of air flow slots, e.g., a first type of slot 955 and a second type of slot 957. The slot 955 can be in the form of a generally up-and-down oriented slot, while the slots 957 are left-to-right slots. The slots 957 are thus arranged so that they are perpendicular to the slot 955. The cover 950 is thus designed to allow the essential oil fragrance to flow out of the ends of the air freshener 600. The rear surface 921 of the housing 910 and the wall 952 are thus parallel to one another when the holder 900 is assembled.

The cover 950 also has a number of locating and retention members for locating and retaining the cartridge 123, 143 in place within the holder 900 and relative to one another and also for releasably locking the cover 950 to the housing 910. For example, the cover 950 can include a pair of locking fingers 967 that include locking tabs 969 at the distal ends thereof. The locking tabs 969 extend radially inward from the inner surface of the cover 950. The housing 910 includes complementary locking structures 971 that mate with the locking fingers 967 for releasably interlocking the cover 950 to the housing 910. For example, along the inner surface of the side wall of the housing 910, a locking rail 973 is formed that includes an opening 975 formed therein. The locking rail 973 is a substantially hollow member and the opening 975 forms an entrance into the interior of the locking rail 973. The interior of the locking rail 973 is sized and shaped so that it can receive the resilient locking finger 967 and in particular, the locking rail 973 rides along and within the interior of the locking rail 973 until the locking tab 969 comes into registration with the opening 975. The natural biasing motion of the locking finger 967 causes the locking tab 969 to engage the opening 975 and the presence of the locking tab 969 within the opening 975 causes the cover 950 be to securely, yet releasably, engaged to the housing 910. To remove the cover 950 from the housing 910, the locking tab 969 is merely depressed within the opening 975 to cause disengagement from the locking rail 973 and therefore permit the cover 950 to be removed from the housing 910.

The housing 910 can include two pairs of opposing slotted rails that are designed to capture and hold one cartridge 123, 143. The rail is an elongated structure (e.g., rectangular cross-section) with a slot formed therein that extends along its length and is open at one end to permit insertion of an object. The spacing between the pairs of rails is designed to allow the pair of cartridges 123, 143 to be inserted and captured within the housing 910 and cover 950 in a spaced, facing relationship. For example, the width of the slot in the rail is selected so that the wall 145 of one cartridge can be inserted therein. The pair of opposite rail are formed so that the opposite ends 145 of the cartridge can be disposed within the slots of the opposite rails and thereby, held in place within the cover 950. When the two cartridges 123, 143 are inserted into the respective slots of the rails, the two cartridges 123, 143 are securely held in place therein with the appropriate amount of spacing between the exposed membranes of each cartridge 123, 143 to permit diffusion of the essential oil. The rails thus permit easy insertion, retention and removal of the cartridges 123, 143 within the housing 910.

The assembled holder 900 is coupled to the air freshener 600 using conventional techniques. For example, the illustrated housing 910 includes the release button 991 which can be in the form of a circular button that is part of a movable finger or tang 993 that is formed in the side wall of the housing 910. For example, the finger 993 is defined by a pair of slots formed in the side wall that extend to a peripheral edge of the side wall. The formation of the pair of slots creates a flexible finger 993 and the button 991 is formed on the outer surface of the flexible finger 993. The left and right front portions 670, 690 of the base 610, which define the two opposing ends of the base 610 include an opening 997 formed therein at or proximate the two ends of the base 610 as shown. The holder 900, in its assembled form, is inserted into one of the respective open ends 612, 614 of the housing 610 and into one of the respective first and fourth compartments 610, 650. As the holder 900 is inserted into the compartment, the button 991 contacts the inner surface of the housing 610 and the resilient nature of the finger 993 causes an inward flexing thereof to allow further insertion of the holder 900 into the base 610. As mentioned above, the guide rails and guide channels (grooves) formed as part of the holder 900 and the base 610, respectively, cause the holder 900 to be inserted into the base 610 in its correct orientation. In other words, when the guide rails mate with the guide channels, the button 991 is axially aligned with the opening 997 such that continued insertion of the holder 900 into the base 610 results in the button 991 mating with the opening 997. As soon as the button 991 is placed in registration with the opening 997, the button 991 moves into engagement with the opening 997 as the stored forces in the flexed finger 993 are released. This results in a mechanical coupling (e.g., snap-fit) between the holder 900 and the assembled air freshener body 610; however, the holder 900 can easily be disengaged and removed from the base 610 by simply pressing down on the button 991 to cause it to disengage from the opening 997 and then pulling the holder 900 out of the air freshener. The holder 900 is ordinarily taken out of the air freshener 600 when replacement of the essential oil substances is needed. In addition, the holder 900 includes vent slots as well as the front cover and therefore, the essential oil fragrance is emitted both from the ends of the air freshener 600 but also from the front cover as well. This provides a better distribution of the essential oil fragrance throughout the room.

As previously mentioned, the air freshener 600 can include a number of different controls and operating modes and can include one or more sensors, e.g., 499. Sensor 499 can be of the type that the air freshener 100 is turned on automatically when the room gets dark and off when the room gets light. Other sensors can likewise be used. In accordance with the present invention, the air freshener 600 offers independent dual functionality where two different fragrances can be emitted in a controlled manner. In other words, since there are two independently operated fan units, two fragrances can be emitted at different, select times based on user inputted instructions or based on a program. For example, a program can be configured to have one fragrance, such as a citrus based essential oil, be emitted during the morning hours, while in the afternoon, a second fragrance is emitted. The time period over which each fragrance is emitted is also based on user input. For example, first fragrance can be emitted over a time period of 1, 2, 3, 4 hours, etc., and then the second fragrance is emitted over a time period of 1, 2, 3, 4 hours, etc. In most operating states, the first and second fragrances are not emitted at the same time but instead, the two fragrances are emitted successively over a period of time. For example, the first fragrance can be emitted for 3 hours and then the second fragrance is emitted for 3 hours. This process can be repeated over the day.

In one embodiment of the present invention, the processor is programmed so that the first and second fan unit can not be operated at the same time in at least some operating modes. As previously discussed, the control panel can include a number of setting, such as a high/low switch which controls fan speed; a fragrance release or cycle time period, such as one hour, three hours or six hours, and a dual setting where the use has placed the same fragrance cartridge in the both ends of the air freshener. Since in the dual setting the same fragrance is being discharged, both fan units can operate during a cycle (e.g., fans can operate in an alternating manner). In addition, the control panel can have different operating modes, such as 24 hour mode (constant operation), night mode where the unit only operates at set times occurring during the night, and day mode where the unit only operates at set times occurring during the day. The day and night modes can operate by means of a light sensor or by programmed time information, such as on and off cycles in comparison to a current time.

The air fresheners 100 and 600 are constructed to be effective for use in standard sized rooms, such as rooms that are up to 1000 sq. feet; however, it will be appreciated that the specifications of the air fresheners 100 and 600 can be altered to tailor the air freshener for use in a particular environment.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. An air freshener comprising:
 a housing having at least a first compartment and a second compartment, each of the first and second compartments having a plurality of first vents formed in the housing;
 a first fan unit disposed within the first compartment;
 a second fan unit disposed within the second compartment;
 a first fragrance emitting substance disposed within the first compartment proximate the first fan unit;
 a second fragrance emitting substance disposed within the second compartment proximate the second fan unit; and
 a programmable processor that is operatively connected to a power source and the first and second fan units and configured to drive the first and second fan units so as to promote discharge of one of the first and second fragrance emitting substances from the housing.

2. The air freshener of claim 1, wherein each of the first and second fragrance emitting substances comprises an essential oil.

3. The air freshener of claim 1, wherein the processor is configured so that the first and second fan units operate independent from one another and at different times and the first and second fragrance emitting substances are different from one another.

4. The air freshener of claim 1, further comprising:
 a first fragrance holder holding the first fragrance emitting substance; and
 a second fragrance holder holding the second fragrance emitting substance;
 wherein the first and second fragrance holders are disposed adjacent the first and second fan units, respectively, within the housing proximate the first vents in the first and second compartments, each of the first and second fragrance holders having a coupling mechanism that permits the holder to be securely held in place within the housing, while at the same time, being selectively removable from the housing.

5. The air freshener of claim 4, wherein each of the first and second fragrance holders includes a base into which the fragrance emitting substance is placed and a cover which is removable coupled to the base, the housing of the air freshener having a first guide feature that mates with a second guide feature that is formed as part of the base to permit the holder to be inserted into the housing in only one orientation.

6. The air freshener of claim 5, wherein the first guide feature comprises a pair of locking rails and the second guide feature comprises a complementary pair of locking channels in which the locking rails are inserted for securely coupling the holder to the housing of the air freshener within the respective compartment.

7. The air freshener of claim 4, wherein the first fragrance emitting substance is contained within at least one cartridge that has a membrane through which the fragrance diffuses and the second fragrance emitting substance is contained within at least one cartridge that has a membrane through which the fragrance diffuses.

8. The air freshener of claim 7, wherein the each of the first and second fragrance emitting substances is held within a pair of cartridges that each has a membrane through which the fragrance diffuses, the pair of cartridges being held within the holder such that the two membranes face another.

9. The air freshener of claim 4, wherein the base includes a depressable button that mates with an opening formed in the housing of the air freshener for securely, yet releasably, coupling the holder to the housing.

10. The air freshener of claim 4, wherein the first fragrance holder is disposed between a first free end of the housing and the first fan unit and the second fragrance holder is disposed between an opposing second end of the housing and the second fan unit, each of the first and second fragrance holders being snap fittingly coupled to the housing with a portion of each holder being accessible along an outer surface of the housing to permit disengagement of the holder from the housing.

11. The air freshener of claim 1, wherein the fan unit includes a rotatable fan blade and the air freshener further includes an air deflector that is located proximate the fan blade below the first vents in the housing and is angled to create air turbulence and direct air moved by the fan blade out of the first vents.

12. The air freshener of claim 1, wherein the processor includes a control panel and is programmed to operate the air freshener in a number of different operating modes and includes a selectable fragrance release or cycle time period in which the fan unit that is proximate to and corresponds to one of the fragrance emitting substances is operated for a programmed amount of time.

13. The air freshener of claim 12, wherein one operating mode comprises a day mode where the air freshener operates only during day light hours and a night mode where the air freshener operates only during night hours.

14. The air freshener of claim 1, wherein the housing includes at least one second vent in each of the first and second compartments, the second vent being an opening formed in the housing, wherein the first vents are located adjacent the respective fan unit and the second vent is located adjacent the respective fragrance emitting substance when the fragrance emitting substance is disposed in a loaded position within the housing.

15. An air freshener comprising:
a housing having at least a first compartment and a second compartment, each of the first and second compartments having a plurality of first vents formed in the housing;
a first fan unit disposed within the first compartment, the first fan unit includes a rotatable first fan blade and the housing further includes a first air deflector that is located proximate the first fan blade below the first vents in the housing and is angled to create air turbulence and direct air moved by the first fan blade out of the first vents;
a second fan unit disposed within the second compartment, the second fan unit includes a rotatable second fan blade and the housing further includes a second air deflector that is located proximate the second fan blade below the first vents in the housing and is angled to create air turbulence and direct air moved by the second fan blade out of the first vents;
a first removable fragrance holder holding a first fragrance emitting substance, the holder having a membrane through which the first fragrance substance diffuses;
a second removable fragrance holder holding a second fragrance emitting substance, the holder having a membrane through which the second fragrance emitting substance diffuses, wherein the first and second fragrance holders are disposed adjacent the first and second fan units located in the first and second compartments, respectively, within the housing proximate the first vents in the first and second compartments, each of the first and second fragrance holders having a coupling mechanism that permits the holder to be securely held in place within the housing in a loaded position, the coupling mechanism including a release structure that permits the holder to be entirely disengaged and removed from the housing to allow access to the fragrance emitting substance; and
a programmable processor that is operatively connected to a power source and the first and second fan units and configured to drive the first and second fan units so as to promote discharge of one of the first and second fragrance emitting substances from the housing.

16. A device for repelling pest comprising:
a housing having at least a first compartment and a second compartment, each of the first and second compartments having vents;
a first fan unit disposed within the first compartment;
a second fan unit disposed within the second compartment;
a first holder including a first fragrance emitting substance disposed within the first compartment proximate the first fan unit;
a second holder including a second fragrance emitting substance disposed within the second compartment proximate the second fan unit; and
a programmable processor that is operatively connected to a power source and the first and second fan units and configured to drive at least one of the first and second fan units so as to promote discharge of one of the first and second fragrance emitting substances from the housing;
wherein at least one of the first and second holders includes a pesticide that is maintained separate from the respective fragrance contained in the same holder.

17. The device of claim 16, wherein the pesticide comprises a liquid insecticide.

* * * * *